US008414891B2

(12) United States Patent
Johns et al.

(10) Patent No.: US 8,414,891 B2
(45) Date of Patent: Apr. 9, 2013

(54) METHOD FOR TREATING PULMONARY HYPERTENSION

(75) Inventors: Roger Johns, Reisterstown, MD (US); Xingwu Teng, Baltimore, MD (US); Dechun Li, Perry Hall, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/211,923

(22) Filed: Aug. 17, 2011

(65) Prior Publication Data

US 2012/0039839 A1 Feb. 16, 2012

Related U.S. Application Data

(62) Division of application No. 12/698,696, filed on Feb. 2, 2010, now Pat. No. 8,080,533, which is a division of application No. 10/543,658, filed as application No. PCT/US2004/003875 on Feb. 9, 2004, now Pat. No. 7,671,037.

(60) Provisional application No. 60/445,594, filed on Feb. 7, 2003.

(51) Int. Cl.
*A61K 39/395* (2006.01)
*A61P 9/12* (2006.01)
*C07K 16/24* (2006.01)

(52) U.S. Cl.
USPC ............... 424/139.1; 530/387.9; 530/841

(58) Field of Classification Search .................. None
See application file for complete search history.

(56) References Cited

U.S. PATENT DOCUMENTS

| 7,309,693 | B2 * | 12/2007 | Egashira et al. | ............ | 514/44 R |
| 2002/0142982 | A1 | 10/2002 | Hla et al. | | |
| 2012/0039839 | A1 * | 2/2012 | Johns et al. | ............ | 424/85.1 |

FOREIGN PATENT DOCUMENTS

| WO | 98-58061 A1 | 12/1998 |
| WO | 99-55868 A2 | 11/1999 |
| WO | 00-04923 A1 | 2/2000 |
| WO | 00-53760 A2 | 9/2000 |
| WO | WO 0189582 A1 * | 11/2001 |

OTHER PUBLICATIONS

Teng et al, 2002 (FASEB Journal, Mar. 20, 2002, 16(4): A75).*
Yamaji-Kegan et al, J Immunol. 2010. 185: 5539-5548.*
Garg, 2008. Diabetic Retinopathy in the Merck Manual, 3 pages as printed.*
International Search Report for International Application No. 504/03875, mailed Aug. 31, 2007.
Branch, AD. TIBS, 1998 vol. 23:45-50.
Downward, J. Science, medicine, and the future. RNA interference. BMJ, 2004 vol. 328:1245-1248.
Lu et al. (2005). Delivering siRNA in vivio for functional genomics and novel therapeutics. From RNA Interference Technology (Cambridge, Appasani, ed., pp. 303-317).
Samarsky et al. (2005). RNAi in drug development: Practical considerations. From RNA Intereference Technology (Cambridge, Appasani, ed., pp. 384-395).
Agrawal et al. Molecular Medicine Today, 2000 vol. 6:72-81.
Chalk et al. Center for Genomics and Bioninformatics, Karolinksa Intitutet. Computational antisense oligo prediction with a neural network model. Dec. 2002. vol. 18:1567-1575.
Ding et al. Nucleic Acids Research. Statistical prediction of single-stranded regions in RNA secondary structure and application to predicting effective antisense target sites and beyond. 2001, vol. 29, No. 5, pp. 1034-1046.
Lehmann et al. Nucleic Acids Research. Theoretical design of antisense genes with statistically increased efficacy. 2000. vol. 28, No. 13, pp. 2597-2604.
Rychahou et al. Department of Surgery and the Sealy Center for Cancer Cell Biology, RNA interference: Mechanisms of action and therapeutic consideration. Nov. 2006. vol. 140, No. 5, pp. 719-725.
Ma et al. American Journal of Respiratory Cell and Molecular Biology, Lipid-Mediated Delivery of Oligonucleotide to Pulmonary Endothelium. 2002. vol. 27:151-159.
Metzger, BioDrug, "Respirable Antisense Oligonucleotide (RASON) Therapy for Allergic Asthma", Oct. 1999; 12 (4): 237-243.
Angelini et al. (Am. J. Physiol. Lung Cell Mol. Physiol, 2009 vol. 296:6582-L593).

* cited by examiner

*Primary Examiner* — Zachary Howard
(74) *Attorney, Agent, or Firm* — Johns Hopkins Technology Transfer (57) ABSTRACT

We found that FIZZ1/RELMα is inducible by hypoxia in lung. The hypoxia-upregulated expression of FIZZ1/RELMα was located in the pulmonary vasculature, bronchial epithelial cells, and type II pneumocytes. Recombinant FIZZ1/RELMα protein stimulates rat pulmonary microvascular smooth muscle cell (RPSM) proliferation dose-dependently. Therefore, we renamed this gene as hypoxia-induced mitogenic factor (HIMF). HIMF strongly activated Akt phosphorylation. The phosphatidylinositol 3-kinase (PI3K) inhibitor LY294002 inhibits HIMF-activated Akt phosphorylation. It also inhibits HIMF-stimulated RPSM proliferation. Thus, the PI3K/Akt pathway, at least in part, mediates the proliferative effect of HIMF. HIMF also has angiogenic and vasoconstrictive activity. Notably, HIMF increases pulmonary arterial pressure and vascular resistance more potently than either endothelin-1 or angiotensin II.

1 Claim, 6 Drawing Sheets

METHOD FOR TREATING PULMONARY HYPERTENSION

CROSS-REFERENCE TO RELATED APPLICATIONS

This application is a divisional of U.S. patent application Ser. No. 12/698,696, filed Feb. 2, 2010, now U.S. Pat. No. 8,080,533, which is a divisional of U.S. patent application Ser. No. 10/543,658, filed Mar. 27, 2006, now U.S. Pat. No. 7,671,037, which is a 35 U.S.C. §371 U.S. national entry of International Application PCT/US2004/003875, having an international filing date of Feb. 9, 2004, which claims the benefit of U.S. Provisional Application Ser. No. 60/445,594, filed Feb. 7, 2003, the contents of each of the aforementioned applications are herein incorporated by reference in their entireties.

This application was made using funds from National Institutes of Health grant HL 39706. The U.S. government therefore retains certain rights in the invention.

FIELD OF THE INVENTION

The invention relates to vasoconstriction, neoangiogenesis, mitogenesis, and vascular remodeling. In particular it relates to an endogenous biological factor that affects these important disease-related processes.

BACKGROUND OF THE INVENTION

FIZZ1 (found in inflammatory zone 1), is a protein induced in murine lung in an ovalbumin-induced asthma model.[1] Besides its induction in the bronchial mucosal epithelial cells, FIZZ1 was also induced in type II pneumocytes and it inhibited NGF-induced survival of DRG neurons and NGF-mediated increase in neuronal CGRP content.[1] Holcomb et al also reported that FIZZ1 is a secreted protein sharing the consensus sequence of 10 cysteine residues in the C-terminus ($^1CX_{11}{}^2CX_8{}^3CX^4CX_3{}^5CX_{10}{}^6CX^7CX^8CX_9{}^9C^{10}C$) with two other murine genes expressed respectively in intestinal crypt epithelial (FIZZ2) and white adipose tissue (FIZZ3) and two related human genes (human FIZZ1 and human FIZZ3).[1] Later, FIZZ3 was shown to be implicated in type II diabetes mellitus and was renamed as resistin.[2] FIZZ1 and FIZZ2 were renamed as resistin-like molecule α (RELMα) and β (RELMβ), respectively.[3] Human FIZZ1, however, was renamed as human RELMβ.[3] Recently, FIZZ1 was found in macrophages[4] and in the stromal vascular fraction of adipose tissue,[5] and it inhibited adipocyte differentiation.[6] However, the function of FIZZ1 remained unclear.

There is a need in the art for effective methods of treating pulmonary hypertension, cancer, cardiac hypertrophy, cardiac ischemia, wounds, and other diseases relating to neoangiogenesis and vasoconstriction.

BRIEF SUMMARY OF THE INVENTION

According to one embodiment of the invention method is provided of promoting wound healing in a patient with a wound. A wound-healing amount of a HIMF protein comprising the amino acid sequence shown in SEQ ID NO: 1 is administered to a patient in need thereof.

According to another embodiment of the invention a method is provided of promoting wound healing in a patient with a wound. A wound-healing amount of an expression construct that encodes HIMF (SEQ ID NO: 1) is administered to a patient in need thereof.

According to yet another embodiment of the invention a method is provided of screening for therapeutic agents. A test agent is contacted with HIMF-treated pulmonary smooth muscle cells. Phosphorylation of Akt is determined A test agent which inhibits HIMF-activated phosphorylation of Akt in the pulmonary smooth muscle cells is identified as a candidate therapeutic agent.

According to an additional embodiment of the invention a method is provided of treating diabetic retinopathy. An antibody which specifically binds to a protein comprising the sequence of SEQ ID NO: 1 is administered to a patient in need thereof in an amount sufficient to relieve symptoms of diabetic retinopathy.

According to yet another embodiment of the invention a method is provided of treating a tumor. An antibody which specifically binds to a protein comprising the sequence of SEQ ID NO: 1 is administered to a patient in need thereof, in an amount sufficient to stop tumor progression.

According to still another embodiment of the invention a method is provided of treating diabetic retinopathy LY294002 is administered to a patient in need thereof, in an amount sufficient to relieve diabetic retinopathy.

According to one more embodiment of the invention a method is provided of treating tumors. LY294002 is administered to a patient in need thereof, in an amount sufficient to stop tumor progression.

According to even another embodiment of the invention a method is provided of treating asthma. LY294002 is administered to a patient in need thereof, in an amount sufficient to relieve asthma-associated symptoms.

According to an embodiment of the invention a method is provided of treating pulmonary hypertension. LY294002 is administered to a patient in need thereof, in an amount sufficient to relieve pulmonary hypertension.

According to yet another embodiment of the invention a method is provided of treating a patient who has or is at risk of heart ischemia. An antibody which specifically binds to a protein comprising the sequence of SEQ ID NO: 1 is administered to the patient in an amount sufficient to reduce the extent of tissue damage to the heart.

According to another embodiment of the invention a method is provided of treating a patient who has or who is at risk of heart ischemia. LY294002 is administered to the patient in an amount sufficient to reduce the extent of tissue damage to the heart.

According to one more embodiment of the invention a method is provided of treating a patient with hypertrophic cardiomyopathy. An antibody which specifically binds to a protein comprising the sequence of SEQ ID NO: 1 is administered to the patient in an amount sufficient to reduce the extent of hypertrophic cardiomyopathy.

According to one embodiment of the invention a method is provided of treating a patient with hypertrophic cardiomyopathy. LY294002 is administered to the patient in an amount sufficient to reduce the extent of hypertrophic cardiomyopathy.

According to yet another embodiment of the invention a method of treating diabetic retinopathy is provided. An antisense construct comprising at least 15 nucleotides of a human HIMF cDNA is delivered to the patient, whereby cells of the patient's retina express an mRNA molecule which is complementary to native HIMF mRNA.

According to one embodiment of the invention a method is provided of treating diabetic retinopathy.

An RNA interference construct comprising at least 19 nucleotides of a human HIMF cDNA is administered to a patient with diabetic retinopathy, whereby cells of the patient's retina express a double stranded RNA molecule, one of whose strands is complementary to native HIMF mRNA.

According to one additional embodiment of the invention a method of treating diabetic retinopathy is provided. siRNA comprising 19 to 21 bp duplexes of a human HIMF mRNA with 2 nt 3' overhangs is delivered to a patient with diabetic retinopathy, whereby HIMF mRNA produced by the patient's retina cells is cleaved.

According to one embodiment of the invention a method is provided for treating diabetic retinopathy. An antisense oligonucleotide comprising at least 15 nucleotides of a human HIMF cDNA is delivered to a patient with diabetic retinopathy, whereby cells of the patient's retina express an mRNA molecule which is complementary to native HIMF mRNA.

According to one embodiment of the invention a method of treating a tumor in a patient is provided. An antisense construct comprising at least 15 nucleotides of a human HIMF cDNA is delivered to a tumor cell, whereby the tumor cell expresses an mRNA molecule which is complementary to native HIMF mRNA.

According to one embodiment of the invention a method is provided of treating a tumor in a patient. An RNA interference construct comprising at least 19 nucleotides of a human HIMF cDNA is administered to a tumor cell in a patient, whereby the tumor cell expresses a double stranded RNA molecule one of whose strands is complementary to native HIMF mRNA.

According to another embodiment of the invention a method is provided of treating tumor in a patient. An siRNA comprising 19 to 21 bp duplexes of a human HIMF mRNA with 2 nt 3' overhangs is administered to a tumor cell in a patient, whereby HIMF mRNA produced by the tumor cell is cleaved.

According to one more embodiment of the invention a method is provided of treating a patient with a tumor. An antisense oligonucleotide comprising at least 15 nucleotides of a human HIMF cDNA is administered to a tumor cell in a patient, whereby the tumor cell expresses an mRNA molecule which is complementary to native HIMF mRNA.

According to one additional embodiment of the invention a method is provided of treating pulmonary hypertension. An antisense construct comprising at least 15 nucleotides of a human HIMF cDNA is delivered to lung cells of a patient with pulmonary hypertension, whereby the patient's lung cells express an mRNA molecule which is complementary to native HIMF mRNA.

According to a further embodiment of the invention a method of treating pulmonary hypertension is provided. An RNA interference construct comprising at least 19 nucleotides of a human HIMF cDNA is delivered to a lung cell of a patient with pulmonary hypertension, whereby the lung cell expresses a double stranded RNA molecule one of whose strands is complementary to native HIMF mRNA.

According to still another embodiment of the invention a method of treating pulmonary hypertension is provided. siRNA comprising 19 to 21 bp duplexes of a human HIMF mRNA with 2 nt 3' overhangs is delivered to a lung cell of a patient with pulmonary hypertension, whereby HIMF mRNA produced by the lung cell is cleaved.

According to one additional embodiment of the invention a method of treating pulmonary hypertension is provided. An antisense oligonucleotide comprising at least 15 nucleotides of a human HIMF cDNA is delivered to a lung cell of a patient with pulmonary hypertension, whereby the lung cell expresses an mRNA molecule which is complementary to native HIMF mRNA.

According to even another embodiment of the invention a method of treating a patient who has or who is at risk of heart ischemia is provided. An antisense construct comprising at least 15 nucleotides of a human HIMF cDNA is delivered to a heart cell of the patient, whereby the heart cell expresses an mRNA molecule which is complementary to native HIMF mRNA.

According to one aspect of the invention a method of treating a patient who has or who is at risk of heart ischemia is provided. An RNA interference construct comprising at least 19 nucleotides of a human HIMF cDNA is delivered to a heart cell of the patient, whereby the heart cell expresses a double stranded RNA molecule one of whose strands is complementary to native HIMF mRNA.

According to one aspect of the invention a method of treating a patient who has or who is at risk of heart ischemia is provided. siRNA comprising 19 to 21 bp duplexes of a human HIMF mRNA with 2 nt 3' overhangs is delivered to a heart cell of the patient, whereby HIMF mRNA produced by the heart cell is cleaved.

According to another aspect of the invention a method of treating a patient who has or who is at risk of heart ischemia is provided. An antisense oligonucleotide comprising at least 15 nucleotides of a human HIMF cDNA is delivered to a heart cell of the patient, whereby the heart cell expresses an mRNA molecule which is complementary to native HIMF mRNA.

According to another aspect of the invention a method of treating hypertrophic cardiomyopathy is provided. An antisense construct comprising at least 15 nucleotides of a human HIMF cDNA is delivered to a heart cell of a patient with hypertrophic cardiomyopathy, whereby the heart cell expresses an mRNA molecule which is complementary to native HIMF mRNA.

According to still one more aspect of the invention a method of treating hypertrophic cardiomyopathy is administered. An RNA interference construct comprising at least 19 nucleotides of a human HIMF cDNA is delivered to a heart cell of a patient with hypertrophic cardiomyopathy, whereby the heart cell expresses a double stranded RNA molecule one of whose strands is complementary to native HIMF mRNA.

According to even one more aspect of the invention a method of treating hypertrophic cardiomyopathy is provided. siRNA comprising 19 to 21 bp duplexes of a human HIMF mRNA with 2 nt 3' overhangs is delivered to a heart cell of a patient with hypertrophic cardiomyopathy, whereby HIMF mRNA produced by the heart cell is cleaved.

According to still one more aspect of the invention a method of treating hypertrophic cardiomyopathy is provided. An antisense oligonucleotide comprising at least 15 nucleotides of a human HIMF cDNA is delivered to a heart cell of a patient with hypertrophic cardiomyopathy, whereby the heart cell expresses an mRNA molecule which is complementary to native HIMF mRNA.

A method is provided for promoting proliferation and differentiation of stem cells. An effective amount of a HIMF protein comprising the amino acid sequence shown in SEQ ID NO: 1 is administered to a population of stem cells. The stem cells thereby proliferate and/or differentiate.

A method is provided for promoting proliferation and differentiation of stem cells. An effective amount of an expression construct that encodes HIMF (SEQ ID NO: 1) is administered to a population of stem cells. The stem cells thereby proliferate and/or differentiate.

A method is provided for promoting proliferation of vascular endothelial cells. An effective amount of a HIMF protein comprising the amino acid sequence shown in SEQ ID NO: 1 is administered to a population of vascular endothelial cells. The vascular endothelial cells thereby proliferate.

A method is provided for promoting proliferation of vascular endothelial cells. An effective amount of an expression construct that encodes HIMF (SEQ ID NO: 1) is administered to a population of vascular endothelial cells. The vascular endothelial cells thereby proliferate.

These and other embodiments of the invention provide the art with methods of alleviating symptoms and causes of serious diseases.

BRIEF DESCRIPTION OF THE DRAWINGS

FIG. 1A shows a time course of HIMF mRNA expression in mouse lung. N, H1d, H4d, H7d, and H3w represent mouse lung exposure to room air (normoxia) or to 10% $O_2$ (hypoxia) for 1, 4, 7, and 21 days, respectively. *$P<0.05$ vs N. FIG. 1B shows a western blot of HIMF. Samples are from mice exposed to normoxia or hypoxia for 4 days. Immunohistochemical staining of HIMF protein in mouse lungs exposed to normoxia (FIG. 1C) or to hypoxia for 4 days (FIG. 1D).

FIGS. 3A-3E shows stimulation of vascular tube formation. Matrigel plugs containing FLAG were stained either with hematoxylin and eosin (HE) (FIG. 3A) or von Willebrand factor (vWF) (FIG. 3B), and matrigel plugs containing HIMF ($5\times10^{-8}$ mol/L) were stained with either HE (FIG. 3C) or vWF (FIG. 3D). The arrowheads point to the newly formed vascular tubes in the matrigel plug.

DETAILED DESCRIPTION OF THE INVENTION

It is a discovery of the present inventors that HIMF is a hypoxia-induced mitogenic factor in lung with potent angiogenic and pulmonary vasoconstrictive properties. The PI3K/Akt pathway, at least in part, mediates its proliferative (mitogenic) effect. These properties render HIMF a useful tool for stimulating wound healing and make inhibition of HIMF a useful tool for treating such disease conditions as diabetic retinopathy, tumors, pulmonary hypertension (with or without allergic or inflammatory involvement), heart ischemia, and hypertrophic cardiomyopathy. Inhibition of HIMF can be done by any method known in the art. These include, without limitation, use of antibodies, antisense oligonucleotides, antisense constructs, RNA interference constructs or siRNA duplex RNA molecules, each of which is specific for HIMF protein or mRNA Inhibitors of downstream events in the HIMF pathway can also be used, as described below.

As is known in the art, supplying a protein to a cell can be done directly by delivering the protein or can be done indirectly by delivering a polynucleotide that encodes the protein. Either method can be used to treat wounds. The protein and/or polynucleotide can be delivered by any means known in the art. It can, for example, be delivered locally to the wounded area. It can alternatively be delivered intravenously. Other methods of delivery, such as oral, peritoneal, subcutaneous, intramuscular, intradermal, and topical, can be used as well. Proteins and/or polynucleotides can be formulated by any means known in the art. For example, liposomes can be used to deliver either proteins or polynucleotides. The coding sequence for HIMF protein can be contained in any useful vector known in the art. Viral or plasmid vectors can be used, for example. Wounds which are amenable to HIMF treatment include, without limitation, those that are caused by injury or surgery. The HIMF that is delivered may be the mature form of the protein or the precursor form. A mature form of the protein in shown in SEQ ID NO: 1 and a precursor form is shown in SEQ ID NO: 2. Proteolytic cleavage converts the precursor form to the mature form. A fusion or conjugated protein comprising the mature protein or precursor protein with additional moieties attached can also be used. For example, moieties with similar or complementary activities can be fused or conjugated to the HIMF sequence.

HIMF protein or polynucleotides encoding its coding sequence can also be administered in vitro or in vivo to stem cells to promote their proliferation and/or differentiation. For example, HIMF accelerates the rate of differentiation of isolated stem cells into striated muscle. In addition, HIMF protein or polynucleotides encoding its coding sequence can be used to stimulate proliferation of vascular endothelial cells. This can be of use to generate sufficient cells of appropriate type to use for tissue engineering purposes, in particular in creating blood vessels. The blood vessels can be used for example, for coronary bypass or replacement of stenosed vessels.

LY294002 is one inhibitor of HIMF-mediated events which is useful for treating diabetic retinopathy, tumors, pulmonary hypertension, heart ischemia, and hypertrophic cardiomyopathy. LY294002, [CAS number 154447-36-6] also known as 2-(4-morpholinyl)-8-phyenyl-4H-1-benzopyran-4-one or 2-(4-morpholinyl)-8-phyenylchromone, is a specific inhibitor of phosphatidylinosotol 3-kinase. Vlahos et al., J. Biol. Chem. 1994, 269:5241-5248. LY294002 inhibits the phosphorylation of Akt.

Antisense constructs, antisense oligonucleotides, RNA interference constructs or siRNA duplex RNA molecules can be used to interfere with expression of HIMF. Typically at least 15, 17, 19, or 21 nucleotides of the complement of HIMF mRNA sequence are sufficient for an antisense molecule. Typically at least 19, 21, 22, or 23 nucleotides of HIMF are sufficient for an RNA interference molecule. Preferably an RNA interference molecule will have a 2 nucleotide 3' overhang. If the RNA interference molecule is expressed in a cell from a construct, for example from a hairpin molecule or from an inverted repeat of the desired HIMF sequence, then the endogenous cellular machinery will create the overhangs. siRNA molecules can be prepared by chemical synthesis, in vitro transcription, or digestion of long dsRNA by Rnase III or Dicer. These can be introduced into cells by transfection, electroporation, or other methods known in the art. See Hannon, G J, 2002, RNA Interference, *Nature* 418: 244-251; Bernstein E et al., 2002, The rest is silence. *RNA* 7: 1509-1521; Hutvagner G et al., RNAi: Nature abhors a doublestrand. *Curr. Opin. Genetics & Development* 12: 225-232; Brummelkamp, 2002, A system for stable expression of short interfering RNAs in mammalian cells. *Science* 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. *Genes & Dev.* 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester W C, and Shi Y. (2002). A DNA vector-based RNAi technology to suppress gene expression in mammalian cells. *Proc. Natl. Acad. Sci. USA* 99(6):5515-5520; Yu J-Y, DeRuiter S L, and Turner D L. (2002). RNA interference by expression of short-interfering RNAs and hairpin RNAs in mammalian cells. *Proc. Natl. Acad. Sci. USA* 99(9):6047-6052.

Antisense or RNA interference molecules can be delivered in vitro to cells or in vivo, e.g., to tumors, eyes, lungs, bronchia, heart, or retina of a mammal. Typical delivery means known in the art can be used. For example, delivery to a tumor can be accomplished by intratumoral injections. Delivery to lung can be accomplished by instillation. Other modes of delivery can be used without limitation, including: intravenous, intramuscular, intraperitoneal, intraarterial, local delivery during surgery, endoscopic, subcutaneous, and per os. In a mouse model, the antisense or RNA interference can be adminstered to a tumor cell in vitro, and the tumor cell can be subsequently administered to a mouse. Vectors can be selected for desirable properties for any particular application. Vectors can be viral or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

HIMF stimulates pulmonary smooth muscle cells and cardiac myocytes to phosphorylate Akt. This is mediated by a phosphatidylinositol 3-kinase (PI3K) enzyme. Inhibitors of this phosphorylation can be used therapeutically to treat diseases such as diabetic retinopathy, tumors, pulmonary hypertension, heart ischemia, and hypertrophic cardiomyopathy. Inhibitors can be found by screening test agents by contacting them with HIMF-treated pulmonary smooth muscle cells. Alternatively, the test agent may be contacted with a cell-free, in vitro system which comprises phosphatidylinositol 3-kinase (PI3K) and Akt. The extent of phosphorylation of Akt can be determined in the presence and absence of the test agent. A test agent which inhibits HIMF-activated phosphorylation of Akt in the pulmonary smooth muscle cells or in the cell-free system can be identified as a candidate therapeutic agent. Phosphorylation of Akt can be determined by any means known in the art. One convenient means employs western blot. Further testing in other model systems or in clinical settings may be performed to confirm inhibitory activity and/or extent of toxicity While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

Materials and Methods

Animals. Sprague-Dawley rats were purchased from Hilltop Lab Animal Inc. (Scottdale, Pa.), and C57BL6 mice were obtained from Charles River Laboratories (Wilmington, Mass.). Housing and procedures involving experimental animals were approved by the Animal Care and Use Committee of the Johns Hopkins University.

Hypoxia exposure. The protocol for the exposure of animals to hypoxia has been previously described1. Briefly, C57BL6 mice aged 8-12 weeks were placed in a Plexiglas chamber maintained at 10% O2 (hypoxic group) or in a chamber open to room air (normoxic group) for specific times with a 12:12-h light-dark cycle. Hypoxia was maintained using a Pro:ox model 350 unit (Reming Bioinstruments, Refield, N.Y.), which controlled fractional concentration of O2 in inspired gas by solenoid-controlled infusion of N2 (Roberts Oxygen, Rockville, Md.) balanced against an inward leak of air through holes in the chamber. The hypoxic mice were exposed to room air for about 10 min daily while their cages were changed. CO2, water vapor, and ammonia were removed by pumping the atmosphere of the hypoxia chamber through Bara Lyme (barium hydroxide lime, USP; Chemetron Medical Division, Allied Healthcare Products, St. Louis, Mo.), Drierite (anhydrous calcium sulfate; Fisher Scientific, Atlanta, Ga.), and activated carbon (Fisher Scientific).

Cell culture and $^3$H-thymidine incorporation assays. Rat pulmonary microvascular smooth muscle cells (RPSM) were isolated from male Sprague-Dawley rats (150-200 g) according to a published method2. Briefly, after the pulmonary artery was flushed with phosphate buffered saline (PBS), it was infused with 2% iron oxide suspension in 0.5% agar. The air spaces were filled with agar, the subpleural margins were harvested and partially collagenase digested, and the microvessels were separated magnetically. The identity of RPSM was confirmed by characteristic appearance on phase-contrast microscopy and indirect immunofluorescent antibody staining for smooth muscle-specific isoforms of β-actin and myosin heavy chain. RPSM were grown in DMEM/F12 medium supplemented with 10% fetal bovine serum (FBS), 2 mM of glutamine, 100 U/ml of penicillin and 100 μg/ml of streptomycin. Passage 3 to 5 cells were used in the experiments.

The cells were seeded in 24-well plates at 5×104/well. After synchronization with serum-free DMEM/F12 (supplemented with 1% Bovine serum albumin (BSA)) for 24 to 48 hours, the cells were treated with the specified agents and 0.1 μCi/well (or 1 μCi/well) of 3H-thymidine in the serum-free DMEM/F12 for 48 hours. After the experimental protocol was completed, the cells were rinsed with PBS twice and incubated in 10% TCA for 30 min. The cells were then washed with PBS two more times and lysed in 250 μl of the lysis buffer (1% SDS, 0.8% NaOH). 3H-thymidine incorporation was measured with a Beckman 6500 scintillation counter in 10 ml of scintillation cocktail.

RT-PCR. One step RT-PCR kit from Qiagen (Valencia, Calif.) was used for the duplex RT-PCR. 0.8 μM each of primers 5'-CAA TCC CAT GGC GTA TAA AAG CAT C-3' (HIMF forward; SEQ ID NO: 5) and 5'-TCA TTC TTA GGA CAG TTG GCA GCA G-3' (HIMF reverse; SEQ ID NO: 6), 0.05 nM each of primers 5'-AAG ATG ACC CAG ATC ATG TTT GAG ACC-3' (β-actin forward; SEQ ID NO: 7) and 5'-GAG CAA TGA TCT TGA TCT TCA TGG TG-3' (β-actin reverse; SEQ ID NO: 8), and 1 µg of total RNA isolated from the murine lung with Tri Reagent (Sigma, St. Louis, Mo.) were used in 50 µl reactions in an iCycler (BioRad, Hercules, Calif.) with the following cycling parameters: 50° C. for 30 min, 95° C. for 15 min, and 28 cycles of 94° C. for 1 min, 55° C. for 30 seconds, and 72° C. for 1 min, followed by 72° C. for 7 min.

Recombinant HIMF. The C-terminal tagged HIMF was generated by PCR and inserted into pcDNA5/FRT/TO vector using the EcoR V and Xho I restriction sites. The pcDNA5/FRT/TO vector containing the recombinant HIMF gene was then integrated in a Flp recombinase-dependent manner into the genome of the Flp-In™ T-REx™ 293 cell line using the Flp-In™ T-REx™ kit from Invitrogen (Carlsbad, Calif.). Production of recombinant HIMF was induced by tetracycline (1 µg/ml) in the 293 cells maintained in DMEM supplemented with 5% FBS, 2 mM of glutamine, 100 U/ml of penicillin and 100 µg/ml of streptomycin, 100 µg/ml of hygromycin B, and 7.5 µg/ml of blasticidin. HIMF was purified by anti-FLAG M2 antibody agarose (Sigma, St. Louis, Mo.) column chromatography from the 293 cell culture medium with FLAG (0.1 mg/ml) elution. The concentration of the HIMF protein was estimated semi-quantitatively by silver staining after SDS-PAGE using BSA as the standard. N-terminal sequencing of the recombinant protein revealed that its N-terminal sequence is DETIEIIVENKVKEL; (SEQ ID NO: 9), suggesting mature HIMF protein has 88 amino acids. Therefore, the recombinant protein has 96 amino acids and has a calculated molecular weight of 10,444 Da. Preliminary experiments revealed that the recombinant protein activated Akt in both RPSM and L2 cells. To exclude the role of possible contaminants such as insulin, a mock isolation control experiment was performed. The medium obtained from the control TREx-293 cell culture was used for the mock isolation. The FLAG elution from the HIMF isolation or the mock isolation were concentrated and washed extensively with PBS by the 20 ml centrifuge filter (3000 MWCO). The HIMF isolation stimulated Akt phosphorylation in the L2 cells. The mock isolation, however, had no effect. The results demonstrated that the effect is HIMF specific and that the recombinant HIMF does not contain insulin, a strong Akt activator. There are conflicting reports about whether or not HIMF exists at higher order forms (dimer or polymer). Banerjee and Lazar reported that recombinant HIMF (RELMα) could not form a dimer3. However, Holcomb et al. showed that the native HIMF (FIZZ1) in the lung homogenate formed higher order forms[4], and Blagoev et al. reported that recombinant HIMF (RELMα) also formed higher order forms5. Our result revealed that HIMF indeed may exist in a dimeric form.

Western blots. The tissue collection and homogenization were performed as described before[1]. HIMF was detected with 1:1000 dilution of the anti-HIMF antibody (raised in rabbit using the peptide CENKVKELLANPANYP (SEQ ID NO: 10) conjugated to keyhole limpet hemocyanin as the antigen) followed by 1:3000 dilution of goat anti-rabbit HRP-labeled antibody (BioRad, Hercules, Calif.). The specificity of the anti-HIMF antibody was preliminarily characterized with peptide competition. The peptide used as the immunogen blocked only the HIMF band and had no effect on the nonspecific bands. For phospho-Akt (pAkt) and Akt blots, RPSM were lysed in CelLytic-M (Sigma, St. Louis, Mo.) supplemented with 1 mM PMSF and 1:100 of protease inhibitor cocktail, phosphatase inhibitor cocktail 1 and 2 (Sigma, St. Louis, Mo.). 18 µg of protein in equal volume was subjected to electrophoresis in 4-20% polyacrylamide gel (Bio-Rad, Hercules, Calif.). After transfer to nitrocellulose membrane, the membrane was first probed with anti-pAkt1/2/3 (Thr308)(1:500, (Santa Cruz Biotechnology, Santa Cruz, Calif.). Then it was stripped and reprobed with anti-Akt1/2/3 (1:500, (Santa Cruz Biotechnology, Santa Cruz, Calif.).

Immunohistochemistry of HIMF. After the mice were sacrificed, the lungs were fixed in 4% formaldehyde in PBS for 2 hours, and 8 µm frozen sections were cut. Following three washes with PBS, the sections were incubated for 1 hour with the anti-HIMF antibody (1:1000 dilution) followed by a 2-hour incubation with goat anti-rabbit antibody conjugated with HRP.

Matrigel plug assays: 200 µl of Matrigel mixed with FLAG or HIMF (50 nM final) was injected subcutaneously (n=3 for each group) on the back of mice. Mice were sacrificed after 7 days and the Matrigel plugs collected. Following fixation in 4% paraformaldehyde in PBS (0.1 mM, pH 7.4), 10 µm frozen sections were cut and stained either with hemotoxylin and eosin (HE) or von Willebrand factor (vWF). For the detection of vWF, anti-human vWF (1:250 dilution, Dako) and anti-rabbit IgG conjugated with FITC (1:500 dilution) were used. The positive cells were counted and expressed as cell numbers per 20× field.

Intact chest mouse experiment. The animals were ventilated with 95% O2/5% CO2 and 2% isoflurane using a custom-designed, constant-flow mouse ventilator with tidal volume set to 6.7 ml/kg at 140 breaths/min. A femoral artery was cannulated for the measurement of systemic arterial pressure, which was measured with a Viggo-Spectramed transducer attached to a polygraph (Grass Instruments, model 7). Heart rate was determined from the systolic pressure pulses with a tachometer (Grass, model 7P44A), and the left jugular vein was cannulated for the administration of drugs. The animals were strapped in the supine position to a fluoroscopic table, and PAP was measured with a specially designed murine pulmonary arterial catheter attached to a pressure transducer (Schneider/Namic). Mean PAP was derived electronically, and pulmonary arterial wedge pressure was determined by recently described procedures[6]. Cardiac output was measured by the thermodilution technique by injection of a known volume (20 µl) of 0.9% NaCl solution at 23° C. into the right atrium and measurement of blood temperature changes in the root of the aorta with a cardiac output computer (Cardiotherm 500, Columbus Instruments, Columbus, Ohio) equipped with a small-animal interface. A thermistor microprobe (Columbus Instruments, Fr-1) was inserted into the right carotid artery and advanced to the aortic arch, where changes in aortic blood temperature were measured.

Rapid amplification of cDNA ends. 5' and 3' Rapid amplification of cDNA ends (RACE) were performed using the SMART RACE cDNA Amplification Kit from Clontech according to the manufacturer's instruction. The messenger RNA isolated from mouse lung was used as the template. Mouse HIMF gene specific primers were designed based on the GenBank sequence (AA712003). 5'-TTA GGA CAG TTG GCA GCA GCG GGC AGT G-3' (SEQ ID NO: 11) and 5'-GAT CCA TCA GCA AAG CCA CAA GCA CAC-3' (nested primer, the underlined nucleotides should be CAG for the positions according to the 3' RACE; SEQ ID NO: 12) were for the 5'RACE; 5'-TCC CTT CTC ATC TGC ATC TCC CTG CTC C-3' (SEQ ID NO: 13) and 5'-CTT GCC AAT CCA GCT AAC TAT CCC TCC AC-3' (nested primer; SEQ ID NO: 14) were for the 3' RACE. *Mus musculus* cDNA clone IMAGE:

1195776 was obtained from ATCC and was sequenced. The mRNA sequence obtained by the 5' and 3' RACE is identical to the IMAGE 1195776.

Cloning of mouse HIMF genomic sequence. 4,159 bp of mouse HIMF genomic sequence was cloned by genome walking using the GenomeWalker kit (Clontech) according to the manufacturer's instruction. The mouse genomic libraries were used as the template. The primers for walking to the 5' direction were 5'-TTAGGACAGTTGGCAG-CAGCGGGCAGTG-3' (SEQ ID NO: 15), 5'-GATCCA-CAGGC AAAGCCACAAGCACAC-3'(SEQ ID NO: 16), and 5'-GGTCTCATCAGTATTCACTGGGACCATC-3' (SEQ ID NO: 17). And the primers for walking to the 3' direction were 5'-CAAGACTATGAACAGA TGGGCCTC-CTGC-3' (SEQ ID NO: 18) and 5'-TGACCATGCAGGGAT-GACTGCTACTGG-3'(SEQ ID NO: 19). The mouse HIMF genomic fragments were cloned into pCR2.1 (Invitrogen) and were sequenced. 4,159 bp of the genomic sequence was assembled and the exon/intron boundaries were determined. The HIMF gene has four exons. Exon 1 is 78 bp; exon 2 is 152 bp; exon 3 is 81 bp; and exon 4 is 287 bp. The translation starts at exon 2, and stops at exon 4. The genomic sequence was deposited into GenBank (AF516926).

Analysis of Nucleic acid motifs. Analyzing the HIMF genomic sequence revealed multiple hypoxia and inflammation related transcription factor binding motifs. According to the consensus sequence TKNNGYAAK[7](SEQ ID NO: 20), six C/EBP binding motifs were found. Among them four were located at the 5' flanking region, and two were at the 3' flanking region. We located five NF-κB motifs (one nucleotide mismatch) according to the consensus sequence GGGRHTYYCC[7] (SEQ ID NO: 21). One was at the 5' flanking region, two were at introns 1 and 2, one was at 3'UTR, and one was at the 3' flanking region. Searching the genomic sequence with the consensus sequence TGASTCAG[4](SEQ ID NO: 22), an AP 1 site was found at 3'UTR. At the intron 3, a putative IRF site (GAAACCAAAAGT; SEQ ID NO: 23) was found matching the consensus sequence GAAASYGA-AASY[7] (SEQ ID NO: 24) 11 out of 12. Searching the genomic sequence with the consensus sequence TTCNNNNGAA (SEQ ID NO: 25), two GAS elements were found. One is located at −87 to −78 bp, which has been demonstrated to be the Stat6 binding site that mediates the IL4-induced promoter activity in myeloid cell line Bmnot cells[8]. Another is located at intron 2.

Statistical analysis. All results are expressed as mean±SEM, and analyzed statistically with either Student t-test or ANOVA followed by Newman post hoc analysis as appropriate. Statistical significance was set as P<0.05.

References for Example 1

1. Quinlan, T R, Li, D, Laubach, V E, Shesely, E G, Zhou, N, Johns, R A. eNOS-deficient mice show reduced pulmonary vascular proliferation and remodeling to chronic hypoxia. *Am J Physiol Lung Cell Mol. Physiol.* 2000; 279:L641-L650.
2. Johnson B A, Lowenstein C J, Schwarz M A, Nakayama D K, Pitt B R, Davies P. Culture of pulmonary microvascular smooth muscle cells from intraacinar arteries of the rat: characterization and inducible production of nitric oxide. *Am J Respir Cell Mol. Biol.* 1994; 10:604-612.
3. Banerjee R R, Lazar M A. Dimerization of resistin and resistin-like molecules is determined by a single cysteine. *J Biol. Chem.* 2001; 276:25970-25973.
4. Holcomb I N, Kabakoff R C, Chan B, Baker T W, Gurney A, Henzel W, Nelson C, Lowman H B, Wright B D, Skelton N J, Frantz G D, Tumas D B, Peale F V, Jr., Shelton D L, Hebert C C. FIZZ1, a novel cysteine-rich secreted protein associated with pulmonary inflammation, defines a new gene family. *EMBO J.* 2000; 19:4046-4055.
5. Blagoev B, Kratchmarova I, Nielsen M M, Fernandez M M, Voldby J, Andersen J S, Kristiansen K, Pandey A, Mann M. Inhibition of adipocyte differentiation by resistin-like molecule 206F α. *J Biol. Chem.* 2002; 277: 42011-42016.
6. Champion, H C, Bivalacqua, T J, D'Souza, F M, Ortiz, L A, Jeter, J R, Toyoda, K, Heistad, D D, Hyman, A L, Kadow-itz, P J. Gene transfer of endothelial nitric oxide synthase to the lung of the mouse in vivo. Effect on agonist-induced and flow mediated vascular responses. *Circ Res.* 1999; 84:1422-1432.
7. Locker J. RNA polymerase II transcription controls of animals: DNA binding sites and transcription factors. In: Locker J, editor. *Transcription Factors. Essential Data.* Chichester, West Sussex John Wiley & Sons; 1996: 13-55.
8. Stutz A M, Pickart L A, Trifilieff A, Baumruker T, Prieschl-Strassmayr E, Woisetschlager M. The Th2 Cell Cytokines IL-4 and IL-13 Regulate Found in Inflammatory Zone 1/Resistin-Like Molecule α Gene Expression by a STATE and CCAAT/Enhancer-Binding Protein-Dependent Mechanism. *J Immunol.* 2003; 170:1789-1796.

Example 2

Overview

Pulmonary vascular remodeling, characterized by pulmonary microvascular smooth muscle cell proliferation, is implicated in the development of hypoxic pulmonary arterial hypertension (PAH). To search for the genes that may participate in the pulmonary remodeling, a cDNA microarray analysis (Incyte Genomics; 9415 genes) was performed using lung samples from mice exposed to 10% $O_2$ or room air for 4 days. EST AA712003 (FIZZ1) was found to be induced by hypoxia.

We hypothesized that FIZZ1 participates in the process of hypoxia-induced pulmonary remodeling. FIZZ1 could be induced at or near the pulmonary vasculature by hypoxia, and the secreted FIZZ1 might have a proliferative effect on the pulmonary vascular smooth muscle cells. We proceeded to validate the microarray result and confirmed that FIZZ1 was markedly induced by hypoxia in the pulmonary vasculature as well as in bronchial epithelial cells and type II pneumocytes. We tested the proliferative role of FIZZ1 in cultured rat pulmonary microvascular smooth muscle cells (RPSM) using a $^3$H-thymidine incorporation assay with recombinant FIZZ1. FIZZ1 was shown to stimulate RPSM proliferation, and so we renamed FIZZ1 as hypoxia-induced mitogenic factor (HIMF).

Example 3

HIMF is Induced in Lung by Hypoxia

Figure 1A:
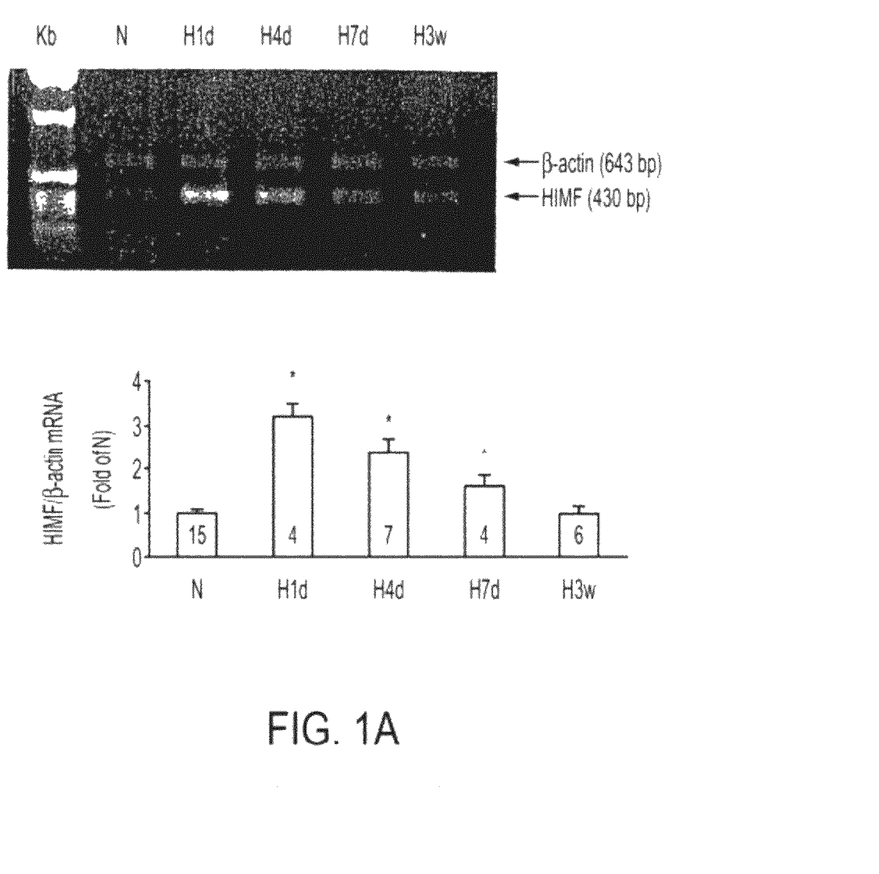
FIGS. 1A to 1D show hypoxia induction of HIMF.

RT-PCR results confirmed that hypoxia upregulated HIMF mRNA expression in murine lungs, and the HIMF mRNA induction peaked at 1 day of hypoxia and lasted for 7 days (FIG. 1A), corresponding with the period of maximum vascular smooth muscle cell proliferation during development of hypoxic PAH.[7]

Figure 1B:
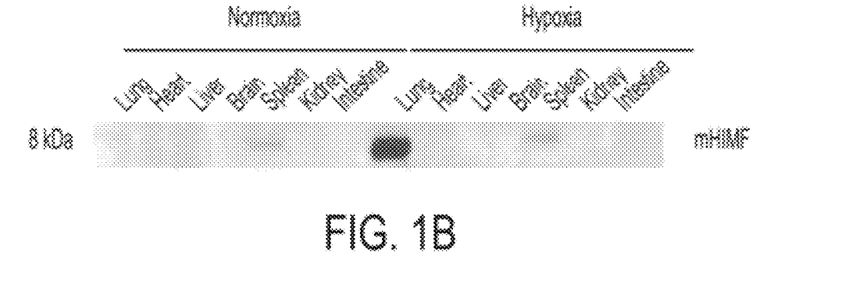
Figure 1C:
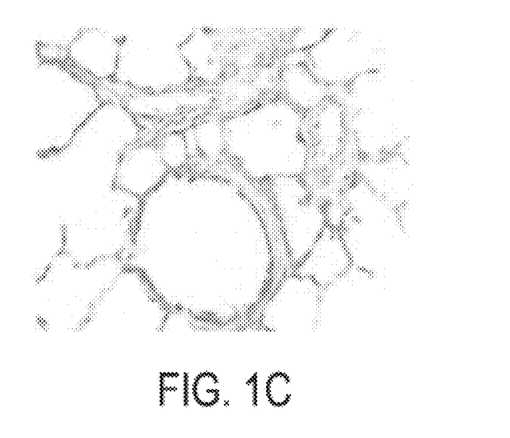
Figure 1D:
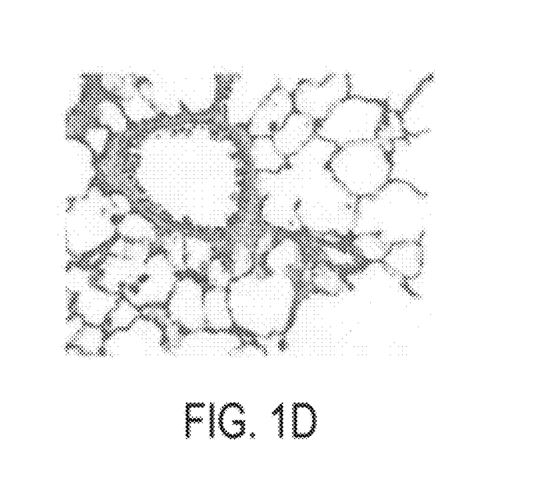
Figure 2A:
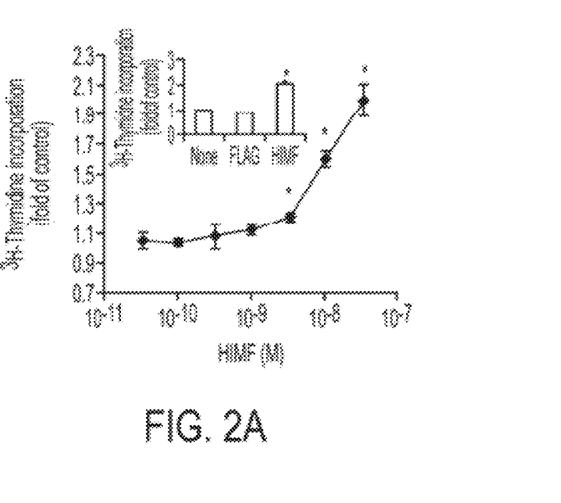
FIG. 2A shows dose-response curve of HIMF-stimulated $^3$H-thymidine incorporation in passage-3 RPSM (5 separate experiments, n=9 to 18). Inset, RPSM were untreated (none) or treated with HIMF ($5\times10^{-8}$ mol/L) or with FLAG. *$P<0.001$ vs untreated.

Western blot shows that exposure of mice to hypoxia for 4 days significantly increased HIMF protein expression only in lung (FIG. 1B). The immunohistochemistry of mouse lung sections showed that, under normoxic conditions, HIMF protein was not expressed in the pulmonary vasculature, and its expression in epithelial cells was minimal (FIG. 1C). Like the ovalbumin-induced asthma model,[1] exposure of mice to hypoxia for 4 days increased HIMF protein expression in airway epithelial cells and type II pneumocytes (FIG. 1D). However, unlike the ovalbumin-induced asthma model[1], hypoxia markedly increased HIMF expression in the pulmonary vascular cells. HIMF is a secreted protein[1] (FIG. 2A). Therefore, our results suggest that under hypoxia, HIMF may be secreted from the pulmonary vascular cells as well as the neighboring type II pneumocytes and act on the pulmonary vascular cells through both paracrine and autocrine fashions.

We cloned and sequenced the genomic sequence of mouse HIMF gene (AF516926). Multiple inflammation-related transcription factor binding motifs such as NF-κB, C/EBP, and GAS were found across the genomic sequence, the 5' and 3' flanking regions and introns, suggesting that the expression of HIMF may be regulated by those transcription factors. The mechanism by which hypoxia upregulates the expression of HIMF in lung remains unknown and is worth investigating.

Example 4

HIMF Stimulates RPSM Proliferation

Figure 2B:
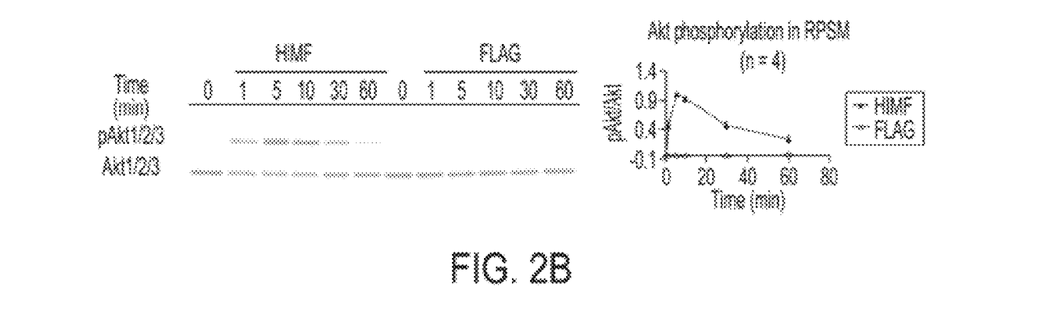
FIG. 2B shows passage-4 RPSM treated with HIFM ($5\times10^{-8}$ mol/L) or with FLAG. The lysates were subject to Western blot for pAkt and Akt.

Chronic hypoxia exposure will result in pulmonary vascular remodeling that is characterized by pulmonary vascular smooth muscle cell migration and proliferation, a major event in the development of hypoxia-induced PAH. We hypothesized that the hypoxia-induced HIMF expression might participate in the pulmonary remodeling. Using a $^3$H-thymidine incorporation assay, the effect of recombinant HIMF on the proliferation of RPSM was tested. FIG. 2B shows that HIMF dose-dependently increased the proliferation of RPSM at concentrations of $3.3 \times 10^{-9}$ to $3.3 \times 10^{-8}$ mol/L, suggesting that HIMF may play a role in the processes of hypoxia-induced pulmonary vascular remodeling. The exact role of HIMF in the processes of hypoxia-induced pulmonary vascular remodeling needs to be evaluated in vivo.

Example 5

Figure 2C:
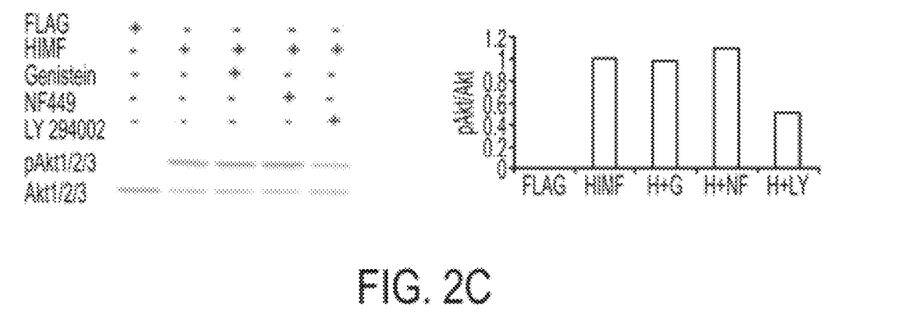
FIG. 2C shows passage-4 RPSM treated with FLAG or HIMF ($5\times10^{-8}$ mol/L) in the absence or presence of genistein (20 µmol/L), NF449 (50 µmol/L), or LY294002 (10 µmol/L) for 5 minutes. The lysates were subjected to Western blot for pAkt and Akt.
Figure 2D:
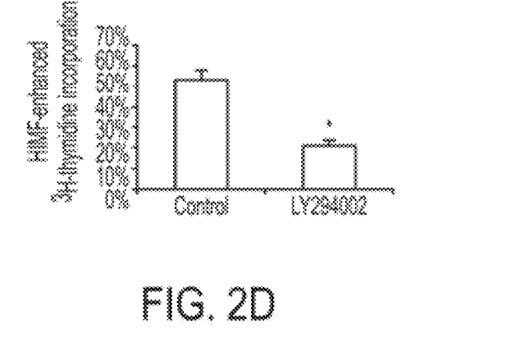
FIG. 2D shows passage-4 RPSM treated with HIMF ($5\times10^{-8}$ mol/L) or FLAG in the absence (Control) or presence of LY294002 (10 µmol/l or 30 µmol/L). n=9 from 4 separate experiments; $P<0.001$ vs Control.

PI3K/Akt Signal Transduction Pathway at Least in Part Mediates the Proliferative Effect of HIMF The phosphatidylinositol 3-kinase (PI3K) family of enzymes is activated by a variety of upstream signals and produces 3' phosphoinositide lipids, which bind to and activate diverse cellular target proteins that ultimately result in the mediation of cellular activities such as proliferation and survival.[8] One of the downstream targets of PI3K is the serine/threonine kinase Aid, which mediates cell growth through stabilization of cyclin D1 and downregulation of Cdk inhibitors p27 and p21.[8] The PI3K/Akt pathway has been shown to mediate proliferation and migration of human pulmonary vascular smooth muscle cells[9] and other vascular smooth muscle cells. To test whether the PI3K/Akt pathway mediates the proliferative effect of HIMF, we first examined whether HIMF could activate the PI3K/Akt pathway. FIG. 2C shows that HIMF strongly activated the phosphorylation of Akt. The Akt activation (phosphorylation) peaked at 5 minutes and was sustained through 60 minutes. The PI3K inhibitor LY294002 (10 μmol/L) inhibited HIMF-activated Akt phosphorylation (FIG. 2D). Genistein (20 μmol/L) and NF449 (50 μmol/L), which have been shown to inhibit serum-induced RPSM proliferation in the preliminary experiments, however, did not inhibit the Akt activation. LY294002 also inhibited HIMF-stimulated RPSM proliferation (FIG. 2E), suggesting that the PI3K/Akt pathway, at least in part, mediates the proliferative effect of HIMF.

Example 6

HIMF Has Angiogenic and Vasoconstrictive Properties

The PI3K/Akt pathway plays a critical role in the regulation of vascular homeostasis and angiogenesis. HIMF activation of the PI3K/Akt pathway suggests that it may have other effects on the vascular cells besides stimulation of RPSM proliferation. The angiogenic effect of HIMF was evaluated in an in vivo Matrigel™ plug model. HIMF significantly increased the vascular tube formation in the Matrigel™ plug in vivo (FIGS. 3A through 3D), from 4.3±0.84 to 17.7±1.37/× 20 field (n=3, P<0.001), suggesting that it is an angiogenic factor. Whether Akt activation participates in the process of HIMF-induced angiogenesis needs further investigation.

Figure 3A:
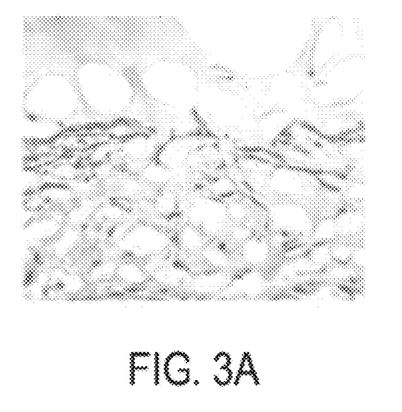
Figure 3B:
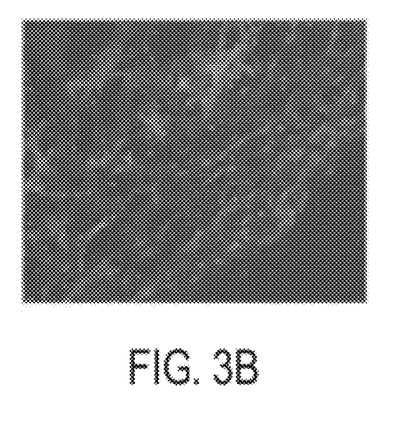
Figure 3C:
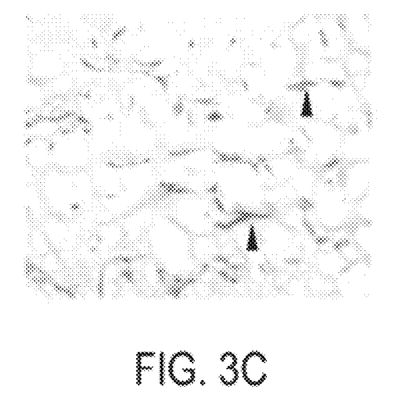
Figure 3D:
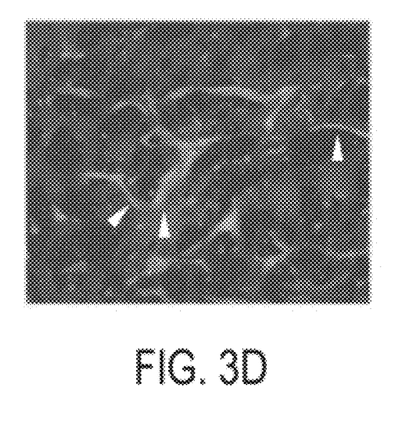
Figure 3E:
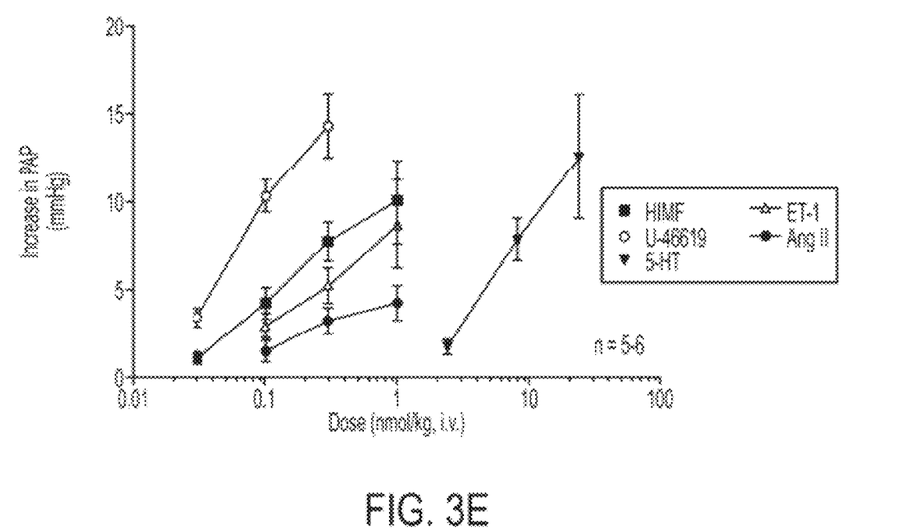
FIG. 3E shows dose-response curves of HIMF and vasoconstricting agents U-46619, endothelin-1 (ET-1), angiotensin II (Ang II), and serotonin (5-HT). The insets are the volume-response curve of the FLAG elution buffer and the graphs of HIMF perfusion on PAP and PVR.

Intravenous injection of HIMF increased the pulmonary arterial pressure (PAP) and pulmonary vascular resistance (PVR) (FIG. 3E). The molar dose-response curves show that HIMF is a more potent pulmonary vasoconstrictor than endothelin-1, angiotensin II, or serotonin (FIG. 3E). Injection of FLAG elution buffer had no effect on PAP, suggesting that the vasoconstrictive effect is HIMF specific. Thus, HIMF is a highly potent constrictor of the pulmonary vasculature. The mechanisms underlying the HIMF-induced constriction and the role of HIMF in pulmonary vascular physiology and pathophysiology require further investigation.

REFERENCES

1. Holcomb 1N, Kabakoff R C, Chan B, Baker T W, Gurney A, Henzel W, Nelson C, Lowman H B, Wright B D, Skelton N J, Frantz G D, Tumas D B, Peale F V Jr, Shelton D L, Hebert C C. FIZZ1, a novel cysteine-rich secreted protein associated with pulmonary inflammation, defines a new gene family. *EMBO J.* 2000; 19:4046-4055.
2. Steppan C M, Bailey S T, Bhat S, Brown E J, Banerjee R R, Wright C M, Patel H R, Ahima R S, Lazar M A. The hormone resistin links obesity to diabetes. *Nature.* 2001; 409:307-312.
3. Steppan C M, Brown E J, Wright C M, Bhat S, Banerjee R R, Dai C Y, Enders G H, Silberg D G, Wen X, Wu G D, Lazar M A. A family of tissue-specific resistin-like molecules. *Proc Natl Acad Sci USA.* 2001; 98:502-506.
4. Raes G, De Baetselier P, Noel W, Beschin A, Brombacher F, Hassanzadeh G G. Differential expression of FIZZ1 and Ym1 in alternatively versus classically activated macrophages. *J Leukoc Biol.* 2002; 71:597-602.
5. Rajala M W, Lin Y, Ranalletta M, Yang X M, Qian H, Gingerich R, Barzilai N, Scherer P E. Cell type-specific expression and coregulation of murine resistin and resistin-like molecule-α in adipose tissue. *Mol. Endocrinol.* 2002; 16:1920-1930.

6. Blagoev B, Kratchmarova I, Nielsen M M, Fernandez M M, Voldby J, Andersen J S, Kristiansen K, Pandey A, Mann M Inhibition of adipocyte differentiation by resistin-like molecule α. *J Biol. Chem.* 2002; 277:42011-42016.
7. Quinlan T R, Li D, Laubach V E, Shesely E G, Zhou N, Johns R A. eNOS-deficient mice show reduced pulmonary vascular proliferation and remodeling to chronic hypoxia. *A m J Physiol Lung Cell Mol. Physiol.* 2000; 279:L641-L650.
8. Katso R, Okkenhaug K, Ahmadi K, White S, Timms J, Waterfield M D. Cellular function of phosphoinositide 3-kinases: implications for development, homeostasis, and cancer. *Annu Rev Cell Dev Biol.* 2001; 17:615-675.
9. Goncharova E A, Ammit A J, Irani C, Carroll R G, Eszterhas A J, Panettieri R A, Krymskaya V P. PI3K is required for proliferation and migration of human pulmonary vascular smooth muscle cells. *Am J Physiol Lung Cell Mol. Physiol.* 2002; 283:L354-L363.

We claim:

1. A method of treating a patient with pulmonary hypertension, comprising: administering to the patient an antibody which specifically binds to a protein comprising the sequence of SEQ ID NO: 1, in an amount sufficient to reduce the extent of pulmonary vasoconstriction.

* * * * *

SEQUENCE LISTING

```
<160> NUMBER OF SEQ ID NOS: 25

<210> SEQ ID NO 1
<211> LENGTH: 88
<212> TYPE: PRT
<213> ORGANISM: Homo sapiens

<400> SEQUENCE: 1

Gln Cys Ser Leu Asp Ser Val Met Asp Lys Lys Ile Lys Asp Val Leu
1               5                   10                  15

Asn Ser Leu Glu Tyr Ser Pro Ser Pro Ile Ser Lys Lys Leu Ser Cys
            20                  25                  30

Ala Ser Val Lys Ser Gln Gly Arg Pro Ser Ser Cys Pro Ala Gly Met
        35                  40                  45

Ala Val Thr Gly Cys Ala Cys Gly Tyr Gly Cys Gly Ser Trp Asp Val
    50                  55                  60

Gln Leu Glu Thr Thr Cys His Cys Gln Cys Ser Val Val Asp Trp Thr
65                  70                  75                  80

Thr Ala Arg Cys Cys His Leu Thr
                85

<210> SEQ ID NO 2
<211> LENGTH: 111
<212> TYPE: PRT
<213> ORGANISM: Homo sapiens

<400> SEQUENCE: 2

Met Gly Pro Ser Ser Cys Leu Leu Leu Ile Leu Ile Pro Leu Leu Gln
1               5                   10                  15

Leu Ile Asn Pro Gly Ser Thr Gln Cys Ser Leu Asp Ser Val Met Asp
            20                  25                  30

Lys Lys Ile Lys Asp Val Leu Asn Ser Leu Glu Tyr Ser Pro Ser Pro
        35                  40                  45

Ile Ser Lys Lys Leu Ser Cys Ala Ser Val Lys Ser Gln Gly Arg Pro
    50                  55                  60

Ser Ser Cys Pro Ala Gly Met Ala Val Thr Gly Cys Ala Cys Gly Tyr
65                  70                  75                  80

Gly Cys Gly Ser Trp Asp Val Gln Leu Glu Thr Thr Cys His Cys Gln
                85                  90                  95

Cys Ser Val Val Asp Trp Thr Thr Ala Arg Cys Cys His Leu Thr
            100                 105                 110

<210> SEQ ID NO 3
<211> LENGTH: 336
<212> TYPE: RNA
<213> ORGANISM: Homo sapiens

<400> SEQUENCE: 3
```

-continued

| | | | | | |
|---|---|---|---|---|---|
| auggggccgu | ccucuugccu | ccuucucauc | cuaaucccc | uucuccagcu | gaucaacccg | 60 |
| gggaguacuc | aguguccuu | agacuccguu | auggauaaga | agaucaagga | uguucucaac | 120 |
| agucuagagu | acagucccuc | uccuauaagc | aagaagcucu | cgugugcuag | ugucaaaagc | 180 |
| caaggcagac | cguccuccug | cccugcuggg | auggcuguca | cuggcugugc | uuguggcuau | 240 |
| ggcugugguu | cgugggaugu | ucagcuggaa | accaccugcc | acugccagug | caguguggug | 300 |
| gacuggacca | cugcccgcug | cugccaccug | accuga | | | 336 |

<210> SEQ ID NO 4
<211> LENGTH: 2318
<212> TYPE: DNA
<213> ORGANISM: Homo sapiens

<400> SEQUENCE: 4

| | | | | | |
|---|---|---|---|---|---|
| ccacgttgtc | ttctttcctt | caccaccacc | caggagctca | gagatctaag | ctgctttcca | 60 |
| tcttttctcc | cagccccagg | acactgactc | tgtacaggat | ggggccgtcc | tcttgcctcc | 120 |
| ttctcatcct | aatccccctt | ctccagctga | tcaacccggg | gagtactcag | tgttccttag | 180 |
| actccgttat | ggataagaag | atcaaggatg | ttctcaacag | tctaggtaac | tgactggggt | 240 |
| aggggaagcg | gggggttgac | ccttgctcat | ttctcctgtt | cttaaactct | agctttgtct | 300 |
| ctatcccatc | ccaagatccc | aaccaagccc | aaccctgat | gagggctttc | tacactaccc | 360 |
| tacccgtgtt | tgaagtcttg | gctaaaagct | gaggttttcc | tgatgaggag | gaagaggtgg | 420 |
| aggagaatgg | tagctgtaat | ttatgaacac | tcattatgaa | ccaggtataa | tccaagtttt | 480 |
| acgtagatta | tttcatttaa | ttcccacaac | cattttatga | ggtaaggaca | actattactt | 540 |
| ctgctttaaa | aatgaggaaa | ctaacccttaa | aagctgatga | gtaggctgat | tctggacaca | 600 |
| gtgtcacctc | caaggtagaa | gacaatttgg | aagggagtaa | ggggattatg | gggaggatag | 660 |
| ctcatgggat | gtaccctttc | ttctttccta | ctcagagtac | agtccctctc | ctataagcaa | 720 |
| gaagctctcg | tgtgctagtg | tcaaaagcca | aggcagaccg | tcctcctgcc | ctgctggtga | 780 |
| gtaactccct | gagagggaat | ggcgactacg | atgccctgta | tcctccctg | tccatctccc | 840 |
| tgcacctacg | tcttccccca | tgtcaggtct | gtatcaccct | ggcaccctgg | ggctgagtca | 900 |
| tgactcttgg | ttcccagaga | cccctttgccc | attcttgttt | ccctgaagga | tgctactggg | 960 |
| ggatcttggg | cttctgcctc | ttcctttcac | cccttcactt | catgcccctg | tttctcagcc | 1020 |
| cttcctctcc | tccattgtcc | cataatgatc | acatacttca | tttctctttc | caatctattc | 1080 |
| ctctgttttg | atgggtaggg | gccaacagag | aggtgaattt | atcacaaatc | gaagaaaact | 1140 |
| gaaactccca | agttccaagt | ctctcacttg | catgagtctc | tttcatggca | gcaaatattt | 1200 |
| gtttctgtga | tttctgtatt | tcttttcttg | aaatgagctc | gcaaaattga | atgagcttga | 1260 |
| ggccccacga | aacctagctc | taccctgac | tgcacagggt | tgaaagatgg | ttgtgggtag | 1320 |
| cccttcctcc | tcttaaattc | caagagctct | gatgtctgtg | cttcatgtgc | tcatgcaggg | 1380 |
| atggctgtca | ctggctgtgc | ttgtggctat | ggctgtggtt | cgtgggatgt | tcagctggaa | 1440 |
| accacctgcc | actgccagtg | cagtgtggtg | gactggacca | ctgcccgctg | ctgccacctg | 1500 |
| acctgacagg | gaggaggctg | agaactcagt | tttgtgacca | tgacagtaat | gaaaccaggg | 1560 |
| tcccaaccaa | gaaatctaac | tcaaacgtcc | cacttcattt | gttccattcc | tgattcttgg | 1620 |
| gtaataaaga | caaactttgt | acctctctgt | gcttatgtca | tctctgttat | tgtccccagc | 1680 |
| ttggggctcc | cctatccaga | aaatgttgtc | agtgtcccag | tggtgacatc | tcagtttggg | 1740 |
| aagtgggatg | ggaagttagg | aaagatatgg | gaagaatggg | aaaacaaac | tgacactcca | 1800 |

```
aacccccact tccctcattt ttatttattt atttatttat tttttcttt ttttcattt    1860 ttttttttt  tattatactc taagttttag ggtacatgtg cacattgtgc aggttagtta   1920
catatgtata catgtgccat gctggtgcgc tgcacccact aacgtgtcat ctagcattag   1980
gtatatctcc caatgctatc cctcccccat ccccgaccc caccacagtc cccagagtgt    2040
gatattcccc ttcctgtgtc cacgtgatct cattgttcaa ttcccaccta tgagtgagaa   2100
tatgcggtgt ttggttttt gttcttgcga tagtttactg agaatgatgg tttccaattt    2160
catccatgtc cctacaaagg acatgaactc atcatttttt atggctgcat agtattccat   2220
ggtgtatatg tgccacattt tcttaatcca gtctatcatt gttggacatt tgggttggtt   2280
ccaagtcttt gctattgtga atagtgccgc aataaaca                          2318
```

```
<210> SEQ ID NO 5
<211> LENGTH: 25
<212> TYPE: DNA
<213> ORGANISM: Homo sapiens

<400> SEQUENCE: 5
caatcccatg gcgtataaaa gcatc                                         25

<210> SEQ ID NO 6
<211> LENGTH: 25
<212> TYPE: DNA
<213> ORGANISM: Homo sapiens

<400> SEQUENCE: 6
tcattcttag gacagttggc agcag                                         25

<210> SEQ ID NO 7
<211> LENGTH: 27
<212> TYPE: DNA
<213> ORGANISM: Homo sapiens

<400> SEQUENCE: 7
aagatgaccc agatcatgtt tgagacc                                       27

<210> SEQ ID NO 8
<211> LENGTH: 26
<212> TYPE: DNA
<213> ORGANISM: Homo sapiens

<400> SEQUENCE: 8
gagcaatgat cttgatcttc atggtg                                        26

<210> SEQ ID NO 9
<211> LENGTH: 15
<212> TYPE: PRT
<213> ORGANISM: Homo sapiens

<400> SEQUENCE: 9

Asp Glu Thr Ile Glu Ile Ile Val Glu Asn Lys Val Lys Glu Leu
 1               5                  10                  15

<210> SEQ ID NO 10
<211> LENGTH: 16
<212> TYPE: PRT
<213> ORGANISM: Homo sapiens

<400> SEQUENCE: 10

Cys Glu Asn Lys Val Lys Glu Leu Leu Ala Asn Pro Ala Asn Tyr Pro
 1               5                  10                  15
```

```
<210> SEQ ID NO 11
<211> LENGTH: 28
<212> TYPE: DNA
<213> ORGANISM: Homo sapiens

<400> SEQUENCE: 11
ttaggacagt tggcagcagc gggcagtg                                          28

<210> SEQ ID NO 12
<211> LENGTH: 27
<212> TYPE: DNA
<213> ORGANISM: Homo sapiens

<400> SEQUENCE: 12
gatccatcag caaagccaca agcacac                                           27

<210> SEQ ID NO 13
<211> LENGTH: 28
<212> TYPE: DNA
<213> ORGANISM: Homo sapiens

<400> SEQUENCE: 13
tcccttctca tctgcatctc cctgctcc                                          28

<210> SEQ ID NO 14
<211> LENGTH: 29
<212> TYPE: DNA
<213> ORGANISM: Homo sapiens

<400> SEQUENCE: 14
cttgccaatc cagctaacta tccctccac                                         29

<210> SEQ ID NO 15
<211> LENGTH: 28
<212> TYPE: DNA
<213> ORGANISM: Homo sapiens

<400> SEQUENCE: 15
ttaggacagt tggcagcagc gggcagtg                                          28

<210> SEQ ID NO 16
<211> LENGTH: 27
<212> TYPE: DNA
<213> ORGANISM: Homo sapiens

<400> SEQUENCE: 16
gatccacagg caaagccaca agcacac                                           27

<210> SEQ ID NO 17
<211> LENGTH: 28
<212> TYPE: DNA
<213> ORGANISM: Homo sapiens

<400> SEQUENCE: 17
ggtctcatca gtattcactg ggaccatc                                          28

<210> SEQ ID NO 18
<211> LENGTH: 28
<212> TYPE: DNA
<213> ORGANISM: Homo sapiens

<400> SEQUENCE: 18
caagactatg aacagatggg cctcctgc                                          28
```

-continued

<210> SEQ ID NO 19
<211> LENGTH: 27
<212> TYPE: DNA
<213> ORGANISM: Homo sapiens

<400> SEQUENCE: 19
tgaccatgca gggatgactg ctactgg        27

<210> SEQ ID NO 20
<211> LENGTH: 9
<212> TYPE: PRT
<213> ORGANISM: Homo sapiens

<400> SEQUENCE: 20

Thr Lys Asn Asn Gly Tyr Ala Ala Lys
 1               5

<210> SEQ ID NO 21
<211> LENGTH: 10
<212> TYPE: PRT
<213> ORGANISM: Homo sapiens

<400> SEQUENCE: 21

Gly Gly Gly Arg His Thr Tyr Tyr Cys Cys
 1               5                  10

<210> SEQ ID NO 22
<211> LENGTH: 8
<212> TYPE: DNA
<213> ORGANISM: Homo sapiens
<220> FEATURE:
<221> NAME/KEY: misc_feature
<222> LOCATION: (4)...(4)
<223> OTHER INFORMATION: s=g or c

<400> SEQUENCE: 22 tgastcag        8

<210> SEQ ID NO 23
<211> LENGTH: 12
<212> TYPE: DNA
<213> ORGANISM: Homo sapiens

<400> SEQUENCE: 23
gaaaccaaaa gt        12

<210> SEQ ID NO 24
<211> LENGTH: 12
<212> TYPE: DNA
<213> ORGANISM: Homo sapiens
<220> FEATURE:
<221> NAME/KEY: misc_feature
<222> LOCATION: (5)...(5)
<223> OTHER INFORMATION: s= g or c
<220> FEATURE:
<221> NAME/KEY: misc_feature
<222> LOCATION: (6)...(6)
<223> OTHER INFORMATION: y= t/u or c
<220> FEATURE:
<221> NAME/KEY: misc_feature
<222> LOCATION: (11)...(11)
<223> OTHER INFORMATION: s= g or c
<220> FEATURE:
<221> NAME/KEY: misc_feature
<222> LOCATION: (12)...(12)
<223> OTHER INFORMATION: y= t/u or c

<400> SEQUENCE: 24

```
gaaasygaaa sy                                                           12

<210> SEQ ID NO 25
<211> LENGTH: 10
<212> TYPE: DNA
<213> ORGANISM: Homo sapiens
<220> FEATURE:
<221> NAME/KEY: misc_feature
<222> LOCATION: (4)...(7)
<223> OTHER INFORMATION: n = A,T,C or G

<400> SEQUENCE: 25 ttcnnnngaa                                                              10
```